US011157601B2

(12) United States Patent
Miu (10) Patent No.: US 11,157,601 B2
(45) Date of Patent: Oct. 26, 2021

(54) ELECTRONIC IDENTITY VERIFICATION (71) Applicant: MorphoTrust USA, LLC, Billerica, MA (US)

(72) Inventor: Stephen Miu, Chelmsford, MA (US)

(73) Assignee: MorphoTrust USA, LLC, Billerica, MA (US)

(*) Notice: Subject to any disclaimer, the term of this patent is extended or adjusted under 35 U.S.C. 154(b) by 254 days.

(21) Appl. No.: 16/054,104

(22) Filed: Aug. 3, 2018

(65) Prior Publication Data

US 2019/0042719 A1 Feb. 7, 2019

Related U.S. Application Data (60) Provisional application No. 62/540,891, filed on Aug. 3, 2017.

(51) Int. Cl.
G06F 21/32 (2013.01)
H04L 9/32 (2006.01)
(Continued)

(52) U.S. Cl.
CPC ............ G06F 21/32 (2013.01); G16H 10/60 (2018.01); H04L 9/321 (2013.01); H04L 9/3231 (2013.01);
(Continued)

(58) Field of Classification Search
CPC ............ G06F 21/32; G06F 2221/2111; G06F 2221/2151; G16H 10/60; G16H 40/20;
(Continued)

(56) References Cited

U.S. PATENT DOCUMENTS 6,154,727 A * 11/2000 Karp .................... G06Q 10/08
705/3
6,591,242 B1 * 7/2003 Karp .................... G16H 40/67
705/2
(Continued)

FOREIGN PATENT DOCUMENTS

CN 108064436 A * 5/2018 ........... H04L 9/0894

OTHER PUBLICATIONS

Yiheng Liang, et al., Identity Verification and Management of Electronic Health Records with Blockchain Technology, Jun. 10-13, 2019, 2019 IEEE International Conference on Healthcare Informatics (ICHI), pp. 1-3.*

(Continued)

Primary Examiner — Farid Homayounmehr
Assistant Examiner — Zhimei Zhu
(74) Attorney, Agent, or Firm — Fish & Richardson P.C.

(57) ABSTRACT

Methods, systems, and apparatus, including computer programs encoded on a computer storage medium, for obtaining identity verification information of a patient. Verifying the patient's identity by: obtaining an indication that the patient identification document is authentic, and verifying that the representation of a biometric of the patient corresponds to a biometric indicated on the patient identification document. Determining that a physical location of a computing device is proximate to a physical location of the patient. In response to verifying the patient and determining that the physical location of the computing device is proximate to the physical location of the patient, determining eligibility of the patient to receive services from the service provider.

20 Claims, 5 Drawing Sheets (51) Int. Cl.
*G16H 10/60* (2018.01)
*H04L 29/06* (2006.01)

(52) U.S. Cl.
CPC ........ *H04L 9/3297* (2013.01); *H04L 63/0853* (2013.01); *H04L 63/0861* (2013.01); *H04L 63/107* (2013.01); *G06F 2221/2111* (2013.01); *G06F 2221/2151* (2013.01); *H04L 63/0884* (2013.01); *H04L 2209/88* (2013.01)

(58) Field of Classification Search
CPC ....... G16H 80/00; H04L 9/321; H04L 9/3231; H04L 9/3297; H04L 63/0853; H04L 63/0861; H04L 63/107; H04L 63/0884; H04L 2209/88
See application file for complete search history.

(56) References Cited

U.S. PATENT DOCUMENTS

| | | | | |
|---|---|---|---|---|
| 8,626,513 | B2* | 1/2014 | Novack | H04L 63/0861 704/273 |
| 9,875,450 | B1* | 1/2018 | Hendrick, III | G06Q 10/0631 |
| 10,331,291 | B1* | 6/2019 | Poder | G06F 21/34 |
| 10,439,815 | B1* | 10/2019 | Poder | H04L 9/12 |
| 10,489,643 | B2* | 11/2019 | Bertan | G06K 9/00449 |
| 10,542,075 | B2* | 1/2020 | Kiukkonen | H04L 63/102 |
| 10,678,939 | B2* | 6/2020 | Eckel | G06F 21/31 |
| 2003/0074228 | A1* | 4/2003 | Walsh | G16H 20/40 705/3 |
| 2003/0094486 | A1* | 5/2003 | Nyfelt | G07F 7/1008 235/375 |
| 2004/0234117 | A1* | 11/2004 | Tibor | G06Q 20/26 382/137 |
| 2005/0097037 | A1* | 5/2005 | Tibor | H04L 63/0861 705/39 |
| 2006/0147093 | A1* | 7/2006 | Sanse | B42D 25/00 382/115 |
| 2006/0157559 | A1* | 7/2006 | Levy | G06Q 20/40145 235/380 |
| 2008/0168062 | A1* | 7/2008 | Reeves | G07C 9/257 |
| 2009/0037225 | A1* | 2/2009 | Burchianti, II | G06Q 10/06 705/3 |
| 2009/0187417 | A1* | 7/2009 | Lidestri | G06Q 30/018 705/317 |
| 2010/0198608 | A1 | 8/2010 | Kaboff et al. | |
| 2011/0000961 | A1* | 1/2011 | McNeal | G06Q 20/3674 235/382 |
| 2011/0145147 | A1* | 6/2011 | Wylie | G06Q 20/40 705/44 |
| 2011/0307272 | A1 | 12/2011 | Kaboff et al. | |
| 2012/0166322 | A1* | 6/2012 | Simon | G06Q 10/1095 705/32 |
| 2013/0151272 | A1* | 6/2013 | Vis | G16H 40/20 705/2 |
| 2013/0159008 | A1* | 6/2013 | Mills | G06Q 10/06 705/2 |
| 2013/0226607 | A1* | 8/2013 | Woody | G06Q 10/063114 705/2 |
| 2013/0262873 | A1* | 10/2013 | Read | H04W 12/06 713/186 |
| 2014/0278486 | A1* | 9/2014 | Moore | G06Q 50/22 705/2 |
| 2014/0278545 | A1* | 9/2014 | Andrews | G16H 10/60 705/3 |
| 2014/0279516 | A1* | 9/2014 | Rellas | G06Q 20/4012 705/44 |
| 2014/0363057 | A1* | 12/2014 | Eckel | G06Q 50/265 382/116 |
| 2015/0058931 | A1* | 2/2015 | Miu | G06Q 20/4016 726/3 |
| 2015/0213213 | A1* | 7/2015 | Havard | G16H 10/20 705/3 |
| 2015/0213304 | A1* | 7/2015 | Passe | G06K 9/00255 382/124 |
| 2015/0228042 | A1 | 8/2015 | Gencarelli et al. | |
| 2015/0278462 | A1* | 10/2015 | Smoley | G06Q 40/08 705/2 |
| 2015/0341370 | A1* | 11/2015 | Khan | H04L 63/0861 726/30 |
| 2015/0356256 | A1* | 12/2015 | Cho | G16H 40/67 705/2 |
| 2015/0363586 | A1* | 12/2015 | Kievan | G06F 21/32 726/19 |
| 2016/0063189 | A1* | 3/2016 | Soon-Shiong | G16H 10/65 705/3 |
| 2016/0210427 | A1* | 7/2016 | Mynhier | G16H 50/20 |
| 2016/0267484 | A1* | 9/2016 | Smoley | G06Q 40/08 |
| 2017/0039502 | A1* | 2/2017 | Guman | G16H 80/00 |
| 2017/0262604 | A1* | 9/2017 | Francois | G06Q 10/0631 |
| 2017/0308983 | A1* | 10/2017 | Hodge | G06Q 50/26 |
| 2018/0053011 | A1* | 2/2018 | East | G16H 40/67 |
| 2018/0103341 | A1* | 4/2018 | Moiyallah, Jr. | G06F 3/04842 |
| 2018/0124047 | A1* | 5/2018 | Fisher | G06F 21/31 |
| 2018/0176017 | A1* | 6/2018 | Rodriguez | H04L 63/0861 |
| 2018/0181964 | A1* | 6/2018 | Zagarese | G06Q 20/40145 |
| 2018/0211724 | A1* | 7/2018 | Wang | G16H 40/20 |
| 2018/0218793 | A1* | 8/2018 | Hebrard | G16H 40/20 |
| 2018/0322352 | A1* | 11/2018 | Phillips | H04W 4/02 |
| 2018/0330814 | A1* | 11/2018 | Auer | G16H 40/20 |
| 2019/0139648 | A1* | 5/2019 | Rutledge | G16H 10/60 |
| 2019/0173873 | A1* | 6/2019 | Brown | H04L 9/3234 |
| 2019/0319795 | A1* | 10/2019 | Kong | H04L 9/14 |
| 2019/0320898 | A1* | 10/2019 | Dirghangi | A61B 3/156 |
| 2020/0042772 | A1* | 2/2020 | Feng | G06K 9/6215 |
| 2020/0082922 | A1* | 3/2020 | Bacastow | H04L 63/10 |
| 2020/0160987 | A1* | 5/2020 | Stewart | G16H 40/20 |
| 2020/0185100 | A1* | 6/2020 | Francois | G06N 5/02 |
| 2020/0286616 | A1* | 9/2020 | Dunn | G16H 50/20 |

OTHER PUBLICATIONS

Stefan Widing, "A Matter of Trust", Apr. 1, 2017, obtained online from <https://www.securityindustry.org/2017/04/01/trusted-identities/>, retrieved on Mar. 27, 2021.*

* cited by examiner

ELECTRONIC IDENTITY VERIFICATION

CROSS-REFERENCE TO RELATED APPLICATION

This application claims the benefit of the filing date of U.S. Provisional Application No. 62/540,891, filed on Aug. 3, 2017. The contents of U.S. Application No. 62/540,891 are incorporated herein by reference in their entirety.

TECHNICAL FIELD

This disclosure generally relates to electronic identify verification.

BACKGROUND

Healthcare providers may provide care to patients in patient homes. The providers may use printed paper schedules to mark down which homes that the provider visited. Providers may include individuals that have undergone specialized education and training, or family members that reside with patients. Existing electronic systems for verifying at home visits to patient are highly susceptible to fraud. For example, existing electronic systems do not verify the physical presence of a home care provide with the patient.

For example, some existing electronic systems currently installed in homes do not ensure that the person providing the services ("caregiver") are who they say they are. Electronic Visit Verification, as mandated in the 21st Century Cures Act, hopes to reduce overall Medicare (subsidized healthcare) costs through focusing on operational efficiency associated with home health care visits and the administration of records, but does nothing to address fraud or attempt to reduce fraud mitigation.

SUMMARY

This specification relates to improvements to identify verification systems to prevent fraud. Implementations of the present disclosure are generally directed to electronic systems, devices, and methods for verifying identifies of and physical presence of two individuals before one another (e.g., a home care provider and a patient).

In general, innovative aspects of the subject matter described in this specification can be embodied in methods that include the actions of obtaining first identity verification information from a first computing device, where the first identity verification information includes an image of a provider identification document and a representation of a biometric of a service provider. The first computing device is associated with a patient. Verifying the service provider by: obtaining an indication that the provider identification document is authentic from a first third party ID verification system, and verifying that the representation of the biometric of the service provider corresponds to a biometric indicated on the provider identification document. Obtaining second identity verification information from a second computing device, where the second identity verification information includes an image of a patient identification document and a representation of a biometric of a patient. The second computing device is associated with the service provider. Verifying the patient by: obtaining an indication that the patient identification document is authentic from a second third party ID verification system, and verifying that the representation of the biometric of the patient corresponds to a biometric indicated on the patient identification document. Determining eligibility of the patient to receive services from the service provider in response to verifying the service provider and the patient. Providing, to the second computing device, access to a record of services to be provided to the patient by the service provider and recording a first time in response to determining the eligibility. Obtaining an indication that the service provider has completed performing the services and, in response, recording a second time from the second computing device. Determining, based on an elapsed time between the first time and the second time, a likelihood that that the service provider properly completed all of the services on the record of services in response to obtaining the indication that the service provider has completed performing the services. Recording completion of the services. Other implementations of this aspect include corresponding systems, apparatus, and computer programs, configured to perform the actions of the methods, encoded on computer storage devices.

These and other implementations can each optionally include one or more of the following features.

In some implementations, the first third party ID verification system is associated with an identification issuing authority that issued the patient identification document and the second third party ID verification system is associated with an identity issuing authority that issued the provider identification document.

In some implementations, determining the eligibility of the patient to receive the services from the service provider includes determining that the service provider is qualified to perform the services.

In some implementations, determining the eligibility of the patient to receive the services from the service provider includes determining that the patient is approved to receive the services from the service provider.

In some implementations, providing access to the record of services to be provided to the patient by the service provider includes identifying a role of the service provider, the role corresponding to a skill set of the service provider, and generating, based on the role, a list of services that the patient is due to receive and that correspond to the role of the service provider.

Some implementations include providing, to the first computing device, access to the record of services to be provided to the patient by the service provider.

In some implementations, determining the likelihood that that the service provider properly completed all of the services on the record of services includes comparing the elapsed time to an expected time for performing the services, and determining the likelihood based on whether the elapsed time is within a threshold value of the expected time.

In some implementations, obtaining the indication that the service provider has completed performing the services includes obtaining third identity verification information, and determining that the third identity verification information includes a second image of the provider identification document and a second biometric of the service provider that matches a corresponding biometric on the provider identification document.

In another general aspect, innovative features of the subject matter described in this specification can be embodied in methods that include the actions of obtaining first identity verification information from a first computing device, where the first identity verification information includes an image of a patient identification document and a representation of a biometric of a patient. The first computing device is associated with a service provider. Verifying the patient by: obtaining an indication that the patient identification document is authentic from a first third party ID verification system, and verifying that the representation of the biometric of the patient corresponds to a biometric indicated on the patient identification document. Determining that a physical location of the computing device is proximate to a physical location of the patient. Determining eligibility of the patient to receive services from the service provider in response to verifying the patient and determining that the physical location of the computing device is proximate to the physical location of the patient. Providing, to the computing device, access to a record of services to be provided to the patient by the service provider and recording a first time in response to determining the eligibility. Obtaining an indication that the service provider has completed performing the services and, in response, recording a second time. Determining, based on an elapsed time between the first time and the second time, a likelihood that that the service provider properly completed all of the services on the record of services in response to obtaining the indication that the service provider has completed performing the services. Recording completion of the services. Other implementations of this aspect include corresponding systems, apparatus, and computer programs, configured to perform the actions of the methods, encoded on computer storage devices.

These and other implementations can each optionally include one or more of the following features.

In some implementations, determining that the physical location of the computing device is proximate to the physical location of the patient includes comparing GPS data associated with the computing device to an address of the patient indicated on the patient identification document.

In some implementations, determining that the physical location of the computing device is proximate to the physical location of the patient includes determining that the GPS data indicates a location that is within a threshold distance of the address.

In some implementations, determining that the physical location of the computing device is proximate to the physical location of the patient includes comparing GPS data associated with the computing device to a predetermined physical location of the patient.

In some implementations, determining that the physical location of the computing device is proximate to the physical location of the patient includes obtaining, from the computing device, a scan of a machine readable code associated with the physical location of the patient.

In some implementations, determining that the physical location of the computing device is proximate to the physical location of the patient includes sending, to a second computing device that is associated with the patient, a machine readable code, and obtaining, from the computing device, a scan of the machine readable code sent to the second computing device.

In some implementations, determining that the physical location of the computing device is proximate to the physical location of the patient includes obtaining, from a second computing device that is associated with the patient, second identity verification information, the second identity verification information including an image of a provider identification document and a representation of a biometric of the service provider, and verifying the service provider by: obtaining an indication that the provider identification document is authentic from a second third party ID verification system, and verifying that the representation of the biometric of the service provider corresponds to a biometric indicated on the provider identification document.

In some implementations, determining the eligibility of the patient to receive the services from the service provider includes determining that the service provider is qualified to perform the services.

In some implementations, the eligibility of the patient to receive the services from the service provider includes determining that the patient is approved to receive the services from the service provider.

In some implementations, providing access to the record of services to be provided to the patient by the service provider includes identifying a role of the service provider, the role corresponding to a skill set of the service provider, and generating, based on the role, a list of services that the patient is due to receive and that correspond to the role of the service provider.

In some implementations, determining the likelihood that that the service provider properly completed all of the services on the record of services includes comparing the elapsed time to an expected time for performing the services, and determining the likelihood based on whether the elapsed time is within a threshold value of the expected time.

These and other implementations can each provide one or more advantages. In some examples, implementations of the present disclosure provided processes that allow an identity verification system to verify both identity of a service provider and patient and the physical presence of the service provider before the patient. Implementations may provide processes for reducing or eliminating fraudulent use of electronic visit verification systems. Implementations can be integrated into any EVV workflow to add accountability seamlessly into the workflow. In some implementations, the accountability of caregiver presence and authorization can be supplemented by confirming the recipient is also present and authorized to receive the supposed services.

The details of one or more implementations of the subject matter described in this specification are set forth in the accompanying drawings and the description below. Other features, aspects, and advantages of the subject matter will become apparent from the description, the drawings, and the claims.

DESCRIPTION OF DRAWINGS

Like reference symbols in the various drawings indicate like elements.

DETAILED DESCRIPTION

Insurance companies such as Medicare may use visit verification to ensure that a qualified care giver visits a homebound patient and administers the assistance required. Visits may be logged with pen and paper on a physical paper schedule, but verifying that the services were performed may be extremely difficult. An insurer or home health care providers, e.g., an organization that is billing Medicare, a hospice, visiting nurses, etc., may require that providers make a phone call from a patient's house to confirm they are at the location. However, not all patients have phones. Additionally, patient signatures may be collected, but sometimes patients are unconscious or otherwise unable to sign.

Electronic visit verification (EVV) can enable the use of a central database, which captures and tallies transactions, and enables automation of reconciliation for the services performed, and then enables an electronic submission of claims from the provider to the insurance company or state agency. Use of a central database or multiple networked databases can enable the ability to use digital data and integrate capture devices and data collection databases, and then run digital data programmatically against other supporting administrative and workflow-management databases, and conditional rules engines, etc.

EVV can use the integration of various input or scanning devices such as magstripe readers (POS terminals), and Integrated Voice Response (IVR) systems. There can also be a supplemental requirement to scan or make a notation of a physical location sensor in order to ensure that a certain route was walked (patrolled), or that a particular postmedical follow-up visit was performed, or that specific para-medical services were performed as part of a contract or insurance mandate. However, "patrolled" routes are typically marked by barcodes or other unique visual representations that are scanned as persons move from location to location and homes may not have such markings. Additionally, confirming a location visited may not confirm that a service was rendered. A gap in the electronic process is "identity verification," or ensuring that the person approved to receive the services are in fact actually receiving the services or a person providing the service is approved, e.g., qualified or certified, to provide the service or type of service required by or approved for the patient.

Identity verification can be integrated in electronic visit verification whereby a government-issued ID such as an ID or driver's license can be used to assert ones identity, and a biometric, e.g., facial, fingerprint, retina, etc., can be processed to ensure the proper assignment of the identity credential itself. In some implementations, the authenticity of the ID is also verified against a third party system (e.g., a system associated with the issuer of the ID). This identity data can be stored locally on a mobile phone of a provider or on a server, or split across both. The data can be in its absolute form, or be hashed and simplified into a tokenized identity to make searches more secure and faster.

By integrating identity verification into the electronic visit verification workflow, much flexibility and programmatic options can be enabled with high confidence that the person performing or receiving the services is who they say they are. The eligibility to receive specific services can be tied to an eligibility database, a provider's credentials and ability to perform the approved tasks can be checked against a provider's or agency database to check for certifications, and a GPS locator on the mobile phone can be used to corroborate the location and timings of the providing the services. In some implementations, the physical co-location of a patient and care giver can be verified electronically by techniques described herein that incorporate machine readable codes, cross-validation techniques, or both. In some implementations, the recipient of the services (e.g., a patient) can be prompted to digitally sign to confirm that the services were rendered.

Identification documents ("ID documents") are broadly defined to include, for example, credit cards, bank cards, phone cards, passports, driver's licenses, network access cards, employee badges, debit cards, security cards, visas, immigration documentation, national ID cards, citizenship cards, permanent resident cards (e.g., green cards), Medicare cards, Medicaid cards, social security cards, security badges, certificates, identification cards or documents, voter registration cards, police ID cards, military ID cards, border crossing cards, legal instruments, security clearance badges and cards, gun permits, gift certificates or cards, membership cards or badges, etc. Also, the terms "document," "card," "badge" and "documentation" are used interchangeably throughout this patent application.

Figure 1A:
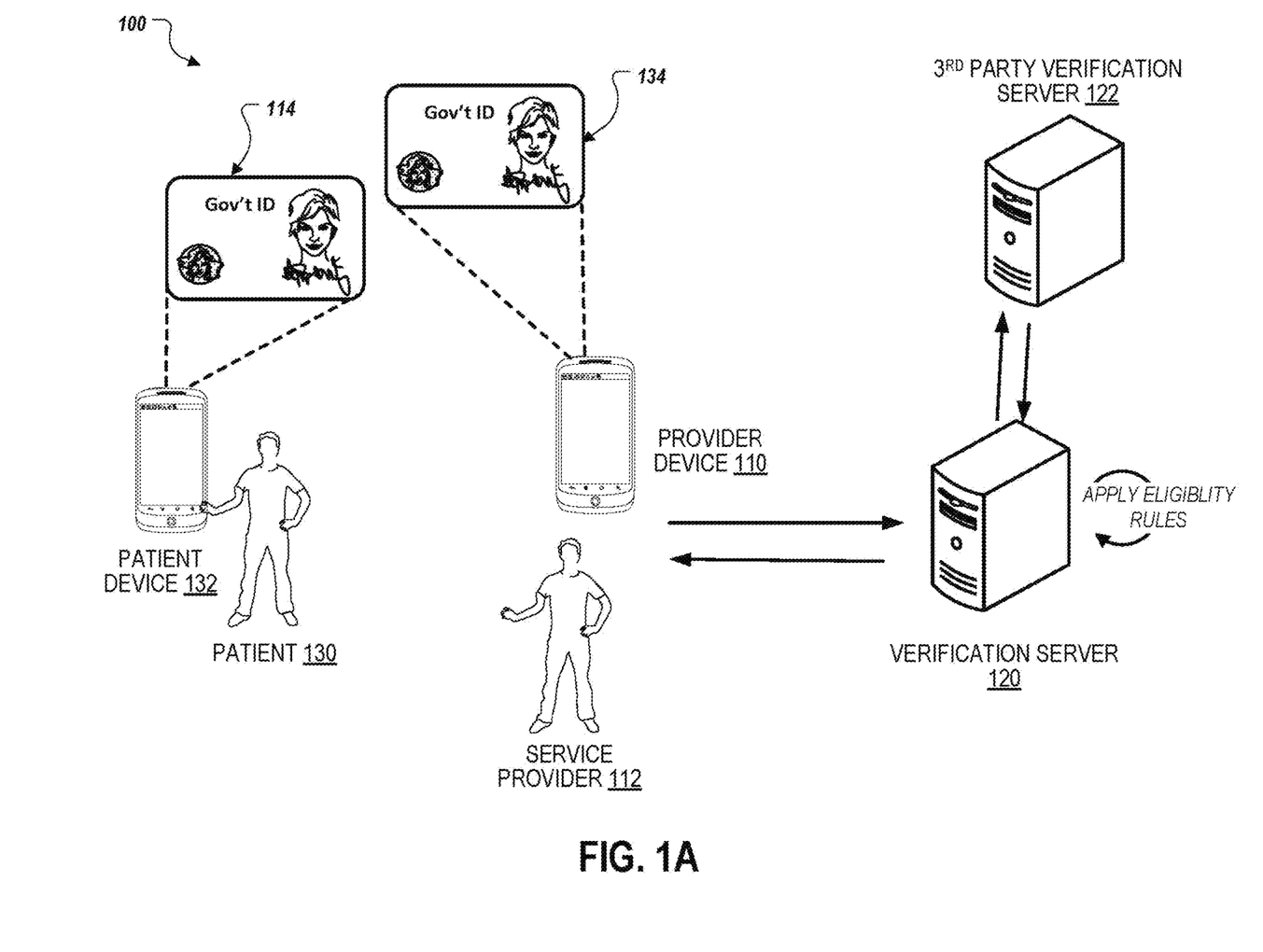
FIG. 1A illustrates an example system using identity verification for electronic visit verification according to implementations of the present disclosure.

FIG. 1A illustrates an example system 100 that uses identity verification for electronic visit verification. The system 100 includes a verification server 120 in communication with a provider device 110, optionally, a patient device 132, and a third party verification server 122. The provider device 110 and the patient device 132 are each associated with a particular user such as service provider 112 (e.g., a home care provider) and a patient 130, respectively.

The verification server 120 and the third party verification server 122 can each be a system of one or more servers. The verification server 120 can be, for example, a secure data server system such as an identity verification system or an EVV server system. The third party verification server 122 can be, for example, a secure data server system that is associated with an identification (ID) issuing entity. For example, the third party verification server 122 can be a government or private server system associated with an ID issuing authority including, but not limited to, a state department of motor vehicles, a security firm, a corporate ID issuing authority, or an immigration department.

The provider device 110 and patient device 132 can be, but is not limited to, a computing device such as a mobile phone, a smartphone, a tablet computer, or a laptop computer. The provider device 110 enables the provider 112 to electronically verify a visit to a patient 130. The provider 112 can be a person that provides services to the patient 130. For example, the provider 112 may be a traveling nurse that performs dialysis on the patient 130.

When a provider 112 arrives at a patient's house, the provider 112 can use a camera included in the provider device 110 to obtain one or more images of an identification document 134 of the patient 130. For example, the provider 112 may ask the patient 130 to present the patient's identification document (e.g., driver's license) and then use the camera of the provider device 110 to obtain an image of a front side and an image of a back side of the patient's driver's license. While a driver's license is used in this example and various examples below, other types of ID documents can similarly be used instead of a driver's license. The provider device 110 can use the images to determine a confidence of an identity of the patient 130. For example, the provider device 110 can determine a 33%, 66%, 100%, or some other confidence that the patient 130 is who they say they are. In some implementations, a second identification document can be scanned to help verify an identity if the confidence scores is below a threshold.

The provider device 110 can determine a confidence of an identity of the patient 130 through verifying (i) that an identification document 134 includes particular visual security features, (ii) that human-readable textual information on a front side of the identification document 134 matches information encoded in a machine-readable code on a back side of the identification document, and (iii) that an image of the patient 130 that the provider 112 captures during the visit using the camera of the provider device 110 matches facial features categorized for the patient 130. For example, the provider device 110 can indicate which of the three checks were successfully passed, a percentage of the checks that were successfully passed, or some other indication of what checks were passed. In some implementations, the provider device 110 can send identification information to the verification server 120 to verify the identity of the patient 130. For example, the identification information can include, but is not limited to, one or more images of the patients identification document (e.g., images of the front and back of the document), a patient biometric such as an image of the patient 130 or an image of a finger print, or a combination thereof.

The particular visual security feature can be a watermark (e.g., a digital watermark), a hologram, a kinegram, laser perforations, or laser ablasions, etc. The human-readable textual information may be one or more of a name, height, and address and the machine-readable code may be a barcode that encodes corresponding information in the barcode. The image of the patient 130 can be an image of the patient's face and the facial features categorized for the patient 130 can be a facial template for a modeled face. For example, the machine-readable code can specify that a face of the person for which the identification document is assigned has a face that is similar to a particular facial template.

The provider device 110 can provide an indication of the confidence to the verification server 120 and, in response, receive an indication whether the provider 112 should provide service to the patient 130. For example, the provider device 110 can provide an indication to the verification server 120 that (i) an identification document does include particular visual security features, (ii) human-readable textual information on a front side of the identification document matches information encoded in a machine-readable code on a back side of the identification document, and (iii) an image of the patient 130 that the provider 112 captures during the visit using the camera of the provider device 110 matches 50% of the facial features categorized for the patient 130 and, in response, receive an indication that the patient 130 is eligible to receive a service from the provider 112.

In another example, the provider device 110 can provide an indication to the verification server 120 (i) that an identification document does not include particular visual security features, (ii) that human-readable textual information on a front side of the identification document matches information encoded in a machine-readable code on a back side of the identification document, and (iii) that an image of the patient 130 that the provider 112 captures during the visit using the camera of the provider device 110 matches 100% of the facial features categorized for the patient 130 and, in response, receive an indication that the patient 130 is not eligible to receive a service from the provider 112.

In some implementations, the provider device 110 can provide a user interface that the provider 112 can use to initially input information that identifies the provider 112. For example, the provider 112 can input a code of a health care provider company with which the provider 112 is associated, in response the provider device 110 can provide a request to the verification server 120 for the names of the individual providers associated with the health care provider company and, in response, receive a list of the providers associated with the health care provider company, display the providers to the provider 112 and then receive a selection by the provider 112 of that provider's name in the list. The provider device 110 can provide the identity of the provider 112 along with the confidence of an identity of the patient 130 to the verification server 120. In some implementations, the provider device 110 can provide a user interface through which the provider 112 can indicate a service to provide and the provider device 110 can also include an indication of the service along with the confidence of the identity of the patient 130.

In some implementations, the provider 112 may be required to verify their own identity to unlock access to the provider device 110 or access to EVV functions (e.g., an EVV app) on the provider device 110. For example, the provider 112 may be required to login-to the provider device 110 by presenting the provider's identification document, similar to the process discussed above with respect to the patient. For example, the provider 112 can use a camera included in the provider device 110 to obtain one or more images of the provider's identification document 114. For example, the provider 112 can use the camera of the provider device 110 to obtain an image of a front side and an image of a back side of the provider's driver's license, and an image of themselves. In some implementations, the provider's identity can be verified by the patient 130 using the patient device 132.

The provider device 110 can output on a display of the provider device the indication whether the provider 112 should provide service to the patient 130. For example, the provider device 110 can output "Identity of patient John Doe sufficiently determined, please go ahead and provide service." In another example, the provider device 110 can output on a display "Identity of patient John Doe insufficiently determined, please re-try verifying identity."

In some implementations, the provider device 110 has the provider 112 indicate services to provide after identity verification. For example, after receiving an indication that the provider 112 can provide service, the provider device 110 can enable the provider 112 to identify on the provider device 110 which services that the provider 112 is providing. The provider device 110 can then transmit that information to the verification server 120 so that the verification server 120 can store data representing that the provider 112 provided the indicated service to the patient 130 at that day and time of indication of providing service.

The verification server 120 can receive an indication of the confidence from the provider device 110 and, in response, provide an indication whether the patient 130 is eligible to receive service from the provider 112. The verification server 120 can determine whether the patient 130 is eligible to receive from the provider 112 based on the confidence of the identity of the patient 130 and eligibility rules. For example, an eligibility rule can be that no services can be provided by that particular provider 112 unless three checks of the patient's identity are satisfied. In another example, an eligibility rules can be that dialysis can be provided by any provider of a particular provider company if two out of three checks are satisfied. Accordingly, some eligibility rules can be dependent on the service to provide and some eligibility rules can be agnostic of the service to provide. The eligibility rules can be stored in an eligibility database that is in communication with the verification server 120.

In some implementations, the verification server 120 can also verify eligibility based on services offered for a patient's insurance plan. For example, the verification server 120 can determine whether the identification documents are for a person with an insurance plan that indicates that dialysis from the provider 112 is covered and only indicate to the provider device 110 that the patient is eligible to receive dialysis if the server 120 determines that the identification documents are for a person with an insurance plan that indicates that dialysis from the provider 112 is covered.

In some implementations, the verification system 120 can also initiate other actions in a federated system. For example, after the verification system 120 determines that provider 110 can provide service to the patient 130, the verification system 120 can automatically provide information on the service to a separate insurance claims processing system and a separate payment processing system. The other separate processing systems can then process an insurance claim and payment based on the information from the verification system 120.

In some implementations, the provider device 110 can use location for electronic visit verification. For example, the provider 112 can open an electronic visit verification application on the provider device 110 when the provider 112 arrives at the patient's house and the application can then cause the provider device 110 to obtain location information through a global positioning system (GPS) sensor of the provider device 110. The application can determine whether the location information is within a threshold proximity (e.g., one eighth, one fourth, half, two or some other number of miles) from an address indicated on the identification document for the patient 130 and only provide the request to confirm eligibility to the verification server 120 if the provider device 110 is within that number of miles. Additionally or alternatively, the provider device 110 can provide the location information to the verification server 120 and the verification server 120 can use an eligibility rules that takes into account location information in determining eligibility. For example, the verification server 120 can determine whether the provider device 110 is at an address of the patient 130 who's ID was scanned.

In some implementations, the system 100 can also include a patient device 132 that the patient 130 can use to verify that the provider 112 is eligible to provide to service to the patient 130. For example, the patient 130 can be worried whether the provider 112 is actually who the provider 112 says they are and are qualified to provide a particular service, and use the patient device 132 to verify that the provider 112 can provide the particular service. Accordingly, the patient device 132 can function similarly to the provider device 110 but instead of scanning the patient's identification document 134, scan the provider's identification document 114 to determine a confidence of the provider's identity, and the verification server 120 can use eligibility rules that consider a confidence of a provider's identity. Alternatively, the provider device 110 can also perform the functions described for the patient device 132 for a patient 130 to verify that the provider 112 is eligible to provide service to the patient 130. For example, the provider 112 can hand the provider device 110 to the patient so that the patient 130 can use it to scan the provider's identification document and take a photo of the provider's face, see that the provider device 110 indicates that the provider's identity is verified and is certified to provide service, and then hand the provider device 110 back to the provider 112. This dual-verification or cross-verification—when the patient 130 uses the patient device 132 to verify provider 112—of provider 112 and patient 130 can further verify that the provider 112 was physically present with the patient 130 and providing service.

In some implementations, the system 100 can be used for other purposes. For example, the system 100 can be used in the context of providing childcare and the provider 112 can be a childcare provider and scan identification documents of parents dropping off their children. The provider device 110 can have providers initially input information that identifies the childcare facility, and then scan the identification document of the parent. The provider device 110 can then provide the confidence of identity and facility information to the verification server 120. The server 120 can then determine whether childcare service is eligible for the parent based on eligibility rules and then provide an indication to the provider device 110 to display to the provider 112. If eligible, the provider device 110 can receive information on children of the parent from the server 120 and then provide options on an interface for the provider 112 to indicate which children of the parent are being dropped off.

Figure 1B:
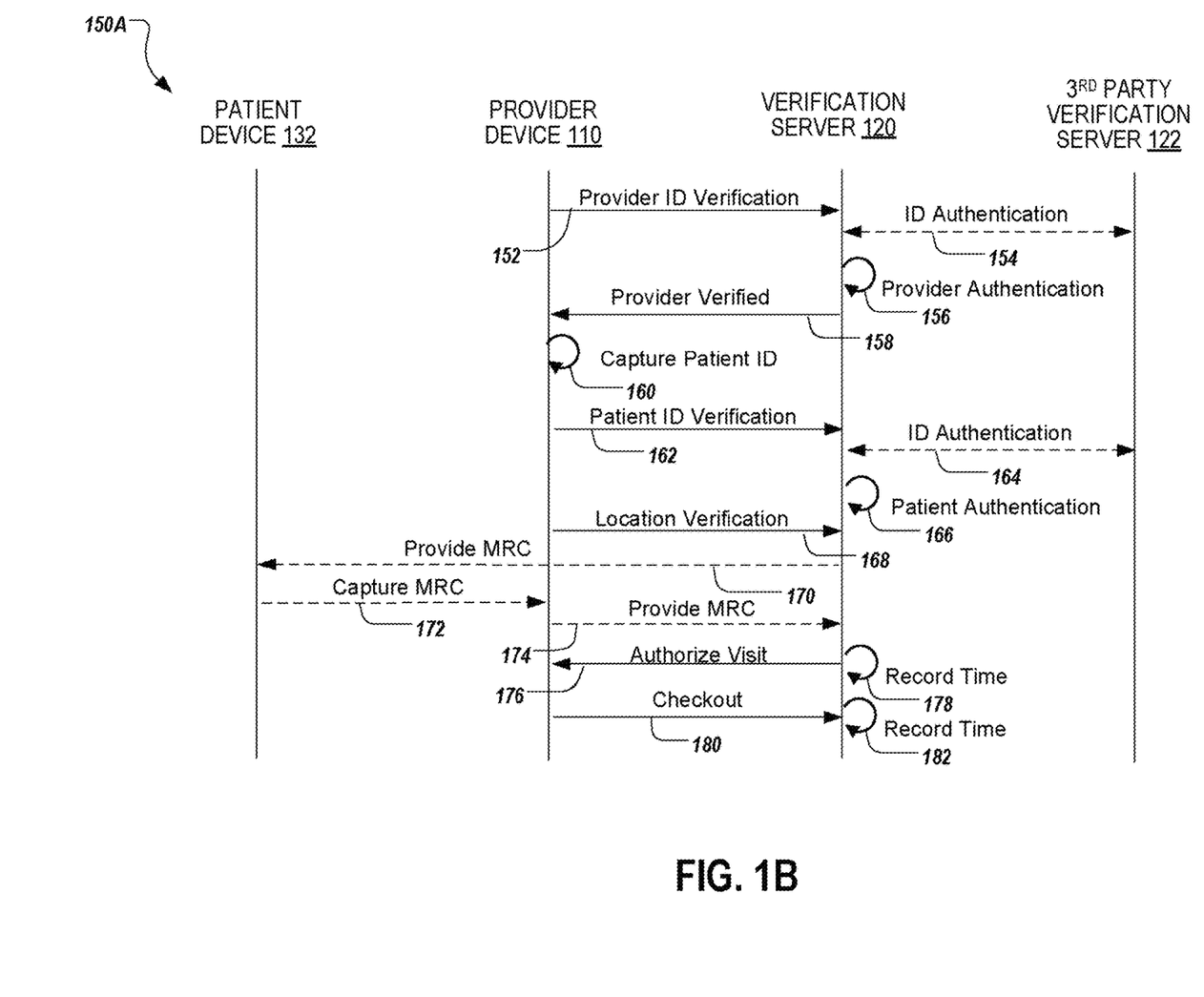
FIGS. 1B and 1C illustrate swim lane diagrams representing exemplary operations of the example system according to implementations of the present disclosure.

FIG. 1B illustrates swim lane diagram representing exemplary operations 150A of the system 100. In reference to FIGS. 1A and 1B, operations 150A permit computing devices to verify identities of parties and the physical co-location of the parties in order to improve operations of electronic visit verification systems and prevent fraud.

The operations 150A may begin with a provider device 110 sending provider ID verification information to verification server 120 (152). For example, a service provider 110 may be required to login or otherwise verify their identity in order to access EVV features stored on provider device 110 (e.g., through a mobile app). The provider ID verification information can include, but is not limited to, login credentials, an image(s) of the service provider's identification document 114, a representation of a biometric of the service provider 110, liveness data associated with the biometric, or a combination thereof. The representation of the service provider's biometric can include, but is not limited to, an image of the service provider's face, an image of a finger print, voice print data, an image of the provider's iris or retina, or a combination thereof.

In some implementations, the verification server 120 conducts ID authentication with the third party verification server 122 (145). This operation may be optional as indicated by the dashed line. For example, the verification server 120 can send the image(s) of the service provider's identification document 114 to the third party verification server 122 to confirm the authenticity of the identification document 114. For example, as discussed above, identification document 114 can include security features which the third party verification server 122 can use to verify that the identification document 114 is authentic. In response, the third party verification server 122 can send data to the verification server 120 that indicates whether the identification document 114 is authentic.

The verification server 120 authenticates the service provider's identity (156). For example, the verification server 120 can authenticate the service provider's identity by authenticating the service provider's login credentials. The verification server 120 can authenticate the service provider's identity by comparing the service provider's biometric information with biometric information on the identification document 114. For example, the verification server 120 can compare an image of the service provider (as included in the service provider ID verification information) to an image (e.g., a portrait) on the identification document 114. As another example, the verification server 120 can compare an image of the service provider's finger print (as included in the service provider ID verification information) to a fingerprint on the identification document 114.

The provider device 110 can be used to capture patient identification information (160). For example, the service provider 112 can use the provider device 110 to capture one or more images of the patient's identification document 134, an image of the patient 130, other biometric information (e.g., a finger print), or a combination thereof. The provider device 110 then sends patient ID verification information to verification server 120 (162). The patient ID verification information can include, but is not limited to, an image(s) of the patient's identification document 134, a representation of a biometric of the patient 130, liveness data associated with the biometric, or a combination thereof. The representation of the patient's biometric can include, but is not limited to, an image of the patient's face, an image of a finger print, voice print data, an image of the patient's iris or retina, or a combination thereof.

In some implementations, the verification server 120 conducts ID authentication with the third party verification server 122 (164). This operation may be optional as indicated by the dashed line. For example, the verification server 120 can send the image(s) of the patient's identification document 134 to the third party verification server 122 to confirm the authenticity of the identification document 134. For example, as discussed above, identification document 134 can include security features which the third party verification server 122 can use to verify that the identification document 134 is authentic. In response, the third party verification server 122 can send data to the verification server 120 that indicates whether the identification document 134 is authentic.

The verification server 120 authenticates the patient's identity (166). For example, the verification server 120 can authenticate the patient's identity by comparing the patient's biometric information with biometric information on the identification document 134. For example, the verification server 120 can compare an image of the patient (as included in the patient ID verification information) to an image (e.g., a portrait) on the identification document 134. As another example, the verification server 120 can compare an image of the patient's finger print (as included in the patient ID verification information) to a fingerprint on the identification document 134.

The provider device 110 can send location verification information to the verification server 120 to permit the verification server 120 to determine the location of the provider device 110, and by extension, the location of the service provider 112. For example, the location information can include GPS data from the provider device 110. The verification server 120 determines the location whether the location of the provider device 110 is sufficiently proximate to a location of the patient 130 to indicate that the service provider 110 is in the physical presence of the patient 130.

The verification server 120 authorizes the visit (176). For example, the verification server 120 can authorize the visit in response to verifying the identity of the patient 130, verifying the identity of the service provider 112, verifying that the location of the provider device 110 is proximate to a physical location of the patient 130, or a combination thereof. In some implementations, the verification server 120 determining the eligibility of the patient 130 to receive services from the service provider 110 before authorizing the visit. For example, the verification server 120 can determine the patient's eligibility based on eligibility rules, as discussed above. In some implementations, the verification server 120 can verify eligibility based on determining that the service provider 110 is qualified to perform services or types of service required by the patient 130. For example, the verification server 120 can determine based on a profile of the service provider which services, if any, the service provider is qualified to perform. For example, a service provider 112 who is a registered nurse may be qualified to perform more complex medical services than a service provider who is a home care assistant. In some implementations, can include a frequency of treatment eligibility variable. For example, a patient may be limited to a particular number of treatments per week or per month, and may not be eligible for the service if that limit has been reached.

In some implementations, the verification server 120 provides the provider device 110 with access to a record of services to be provided to the patient 130 in response to authorizing the visit. For example, the verification server 120 can provide checklist of services for the service provider 110 to perform during the visit. For example, the verification server 120 generates the record of services that the service provider 112 is to provide to the patient 130 based on a role of the service provider 112. For example, the service provider's role may correspond to a skill set of the service provider. The role can indicate type of services that each service provider is eligible to perform. The verification server 120 can generate the list of services for the service provider 112 to perform based on comparing services that the service provider is eligible to perform in accordance with their role, to a list of services that the patient 130 needs and/or is approved or scheduled to receive.

In some implementations, the record of services to be provided to the patient 130 by the service provider 112 is also sent to the patient device 132. For example, the record of service can be provided to the patient device 132 so that the patient 130 has access to an independent list of the services the service provider 112 has been authorized to conduct.

In addition the verification server 120 can record the time that the services begin upon authorizing the visit (178). The time that the service provider 112 begins performing the services can be used, as described below, to verify whether the service provider 112 completes all of the services.

The provider device 110 sends an indication that the service provider has completed performing the services to the verification server 120. For example, when the service provider 112 has completed all the services required for the visit, they may be required to "checkout" of the visit using the provider device 110. In some implementations, the checkout can require the service provider to re-submit their identification information. For example, the service provider 112 may be required to resubmit images of their identification document 113 and biometric information (e.g., an image of their face or fingerprint). In response to receiving the checkout indication, the verification server 120 records the time that the services were completed. The verification server 120 can compute the elapsed time of the visit from the recorded start time and end time of the visit and determine a likelihood that that the service provider properly completed all of the services on the record of services.

Finally, the verification server can record the completion of the visit. For example, the verification server can store metadata related to the transaction. The metadata can include, but is not limited to, the identity of the patient; the identity of the service provider; data from the identification documents of either the patient, the service provider, or both; data related to the services provided; the start and finish times; and the total elapsed time of the visit. In some implementations, the transaction metadata can be uploaded to eligibility database.

Figure 1C:
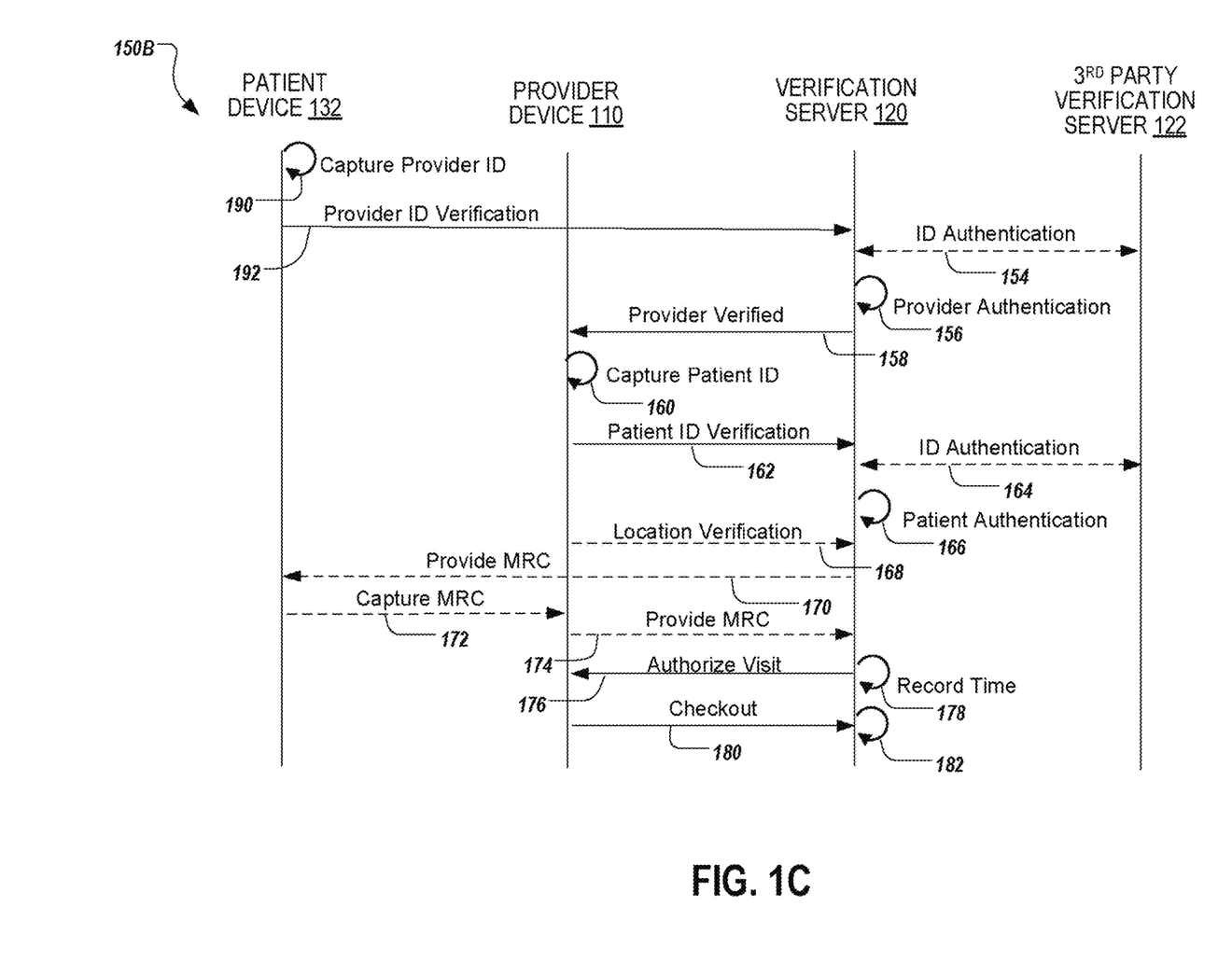

FIG. 1C illustrates swim lane diagram representing exemplary operations 150B of the system 100 that include cross-verification between the service provider 112 and the patient 130. The operations 150B are similar to operations 150A except for the steps 190 and 192. Specifically, operations 150B provide for cross-verification of identities between the service provider 112 and the patient 130. The cross-verification allows the system 100 to establish, with a high degree of confidence, that the service provider 112 is in the physical presence of the patient 130. Because the cross-verification provided by steps 190, 192, 160, and 162 can serve as an indication that the service provider 112 is in the physical presence of the patient 130, step 168 may be optionally performed.

The cross-verification is performed when, the patient device 132 is used to verify the identity of the service provider 112 and the provider device 110 is used to verify the identity of the patient 130. For example, the patient device 132 can be used to capture the identification of the service provider 112 (190). For example, the patient 130 can use the patient device 132 to capture one or more images of the service provider's identification document 114, an image of the service provider 112, other biometric information (e.g., a finger print), or a combination thereof. The provider device 110 then sends provider ID verification information to verification server 120 (192). The provider ID verification information can include, but is not limited to, an image(s) of the service provider's identification document 114, a representation of a biometric of the service provider 112, liveness data associated with the biometric, or a combination thereof. The representation of the service provider's biometric can include, but is not limited to, an image of the service provider's face, an image of a finger print, voice print data, an image of the service provider's iris or retina, or a combination thereof. The verification server 120 then verifies the identity of the service provider 112 as described above in reference to steps 154-158. The service provider 112 verifies the identity of the patient according to steps 160-166 as described above.

In some implementations, the positive verification of the provider's identity through the patient device 132 can serve as a login step for the service provider 112 to be granted access to EVV functions on the provider device 110. After being granted access, the service provider 112 can verify the identity of the patient according to steps 160-166 as described above.

In reference to the operations of FIGS. 1B and 1C, in some implementations, the verification server 120 can determine that the physical location of the provider device 110 is proximate to the physical location of the patient by comparing GPS data associated with the provider device 110 to an address of the patient. For example, the verification server 120 can obtain the patient's address from the patient's identification document, the previous care records of the patient, insurance records, or a patient account. In some implementations, the verification server 120 determines whether the GPS location of the provider device 110 is within a threshold distance of the patient's known address.

In some implementations, the physical presence of the service provider 112 before the patient 130 can be determined using machine readable codes. For example, a unique machine readable code can be provided to the patient 130. In order to verify their physical presence before the patient 130, the service provider 112 may be required to scan the machine readable code using the provider device 110. Referring to FIGS. 1B and 1C steps 170-174, location verification using an machine readable code can be performed by the verification server 120 sending a patient specific machine readable code to the patient device 132 (170). The machine readable code can be generated and sent prior to the visit, for example, at a time when the patient registers for home health care visits. In some examples, the machine readable code can be generated and sent to the patient device 132 in response to the provider device 110 requesting location verification (168).

For example, the verification server 120 can generate a machine readable code. The verification server 120 can generate that is unique to the particular patient and/or unique to the particular visit. In some examples, the machine readable code is an alphanumeric code that is unique to the patient and/or the particular visit. For example, the authorization credential can be a pseudo random code that is generated in response to the location verification request of the provider device 110.

For example, the machine readable code can be an optical machine-readable code, sound-based machine-readable code, an out-of-band communication signal (e.g., Bluetooth or Zigbee) or an electromagnetic machine-readable code (e.g., a Near-Field Communication (NFC) signal). For example, an optical machine readable code encodes data such as an alphanumeric authorization credential in a spatially varying graphical code (e.g., a QR code or a bar code). An optical machine readable code can be displayed on one computing device and captured by scanning the machine readable code with another computing device to obtain an image of the code (e.g., by a camera). For example, sound-based machine readable code can be a sound signal that is modulated to encode data such as an alphanumeric authorization credential. The sound signal representation of the credential can be output through a speaker of a computing device and received by a microphone of another computing device. For example, an electromagnetic machine readable code can encode data such as an alphanumerical authorization credential in an NFC signal generated by one computing device and received by an NFC reader on another computing device.

The service provider 112 can scan the machine readable code (172). For example, the provider device 110 can be used to scan an image of the machine readable code presented on the patient device 132, or to scan a printed copy of the machine readable code posted in the patients' home. If the machine readable code is an audio machine readable code or an NFC, the provider device 110 can be used to capture the audio signals as presented by the patient device 132 or to capture the radio signals of the NFC. The provider device 110 then transmits the scanned machine readable code to the verification server 120 (174). The verification server 120 compares the scanned machine readable code as received from the provider device 110 to the machine readable code that was sent to the patient device 132 to verify that the service provider is in the presence of the same patient to whom the machine readable code was originally sent.

Furthermore, the sequence of the operations 150A and 150B shown in FIGS. 1B and 1C are not intended to be limiting. In some implementations, operations can be executed in a different sequence, operations can be omitted, or both. In addition, the operations 150A, 150B can be performed by devices other than those indicated in FIGS. 1B and 1C. For example, in some implementations, some or all of the identify verification operations be performed locally on provider device 110 or patient device 132, with fewer of the identity verification operations being performed by verification server 120.

Figure 2:
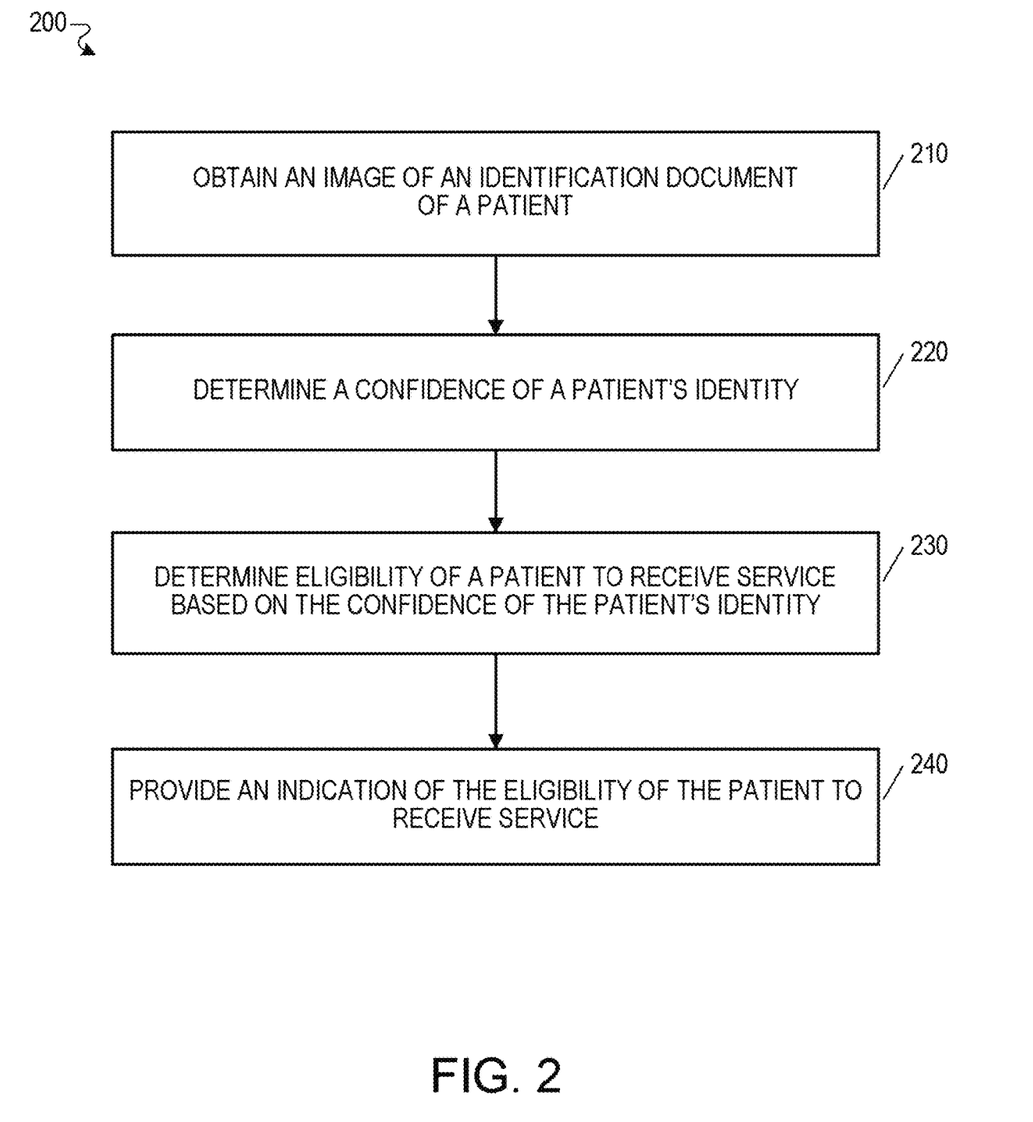
FIG. 2 is a flowchart of an example process using identity verification for electronic visit verification.

FIG. 2 is a flowchart of an example process 200 using identity verification for electronic visit verification. The operations of the process 200 can be performed by one or more computing systems, such as the provider device 110, patient device 132, and/or verification server 120 of the system 100 shown in FIG. 1. In some examples, the example process 200 can be provided by one or more computer-executable programs executed using one or more computing devices. For example, the example process 200, or portions thereof, can be provided by one or more programs executed by a computing system (e.g., verification server 120, provider device 110, or patient device 132).

The process 200 includes obtaining an image of an identification document of a patient (210). For example, the provider 112 can launch an electronic visit verification application on the provider device 110, the application can prompt the provider 112 to scan a driver's license of the patient 130, and the provider 112 can then use the provider device 110 to obtain images of the front and back of the patient's driver's license. A biometric of the patient can also be obtained. For example, the application can also prompt the provider 112 to obtain a biometric of the patient, e.g., take a photo of the patient's face, finger, or retina, etc.

The process 200 includes determining a confidence of a patient's identity (220). For example, the provider device 110 can determine which security checks for an identification document of the patient 130 are satisfied based on the images captured of the identification document and a biometric, e.g., from an image of the patient's face, captured during the visit of the patient 130. Determining the confidence of the patient's identity can include determining a confidence score that reflects a likelihood that the patient is the person to whom the identification document was issued.

The process 200 includes determining an eligibility of a patient to receive service based on the confidence of the patient's identity (230). For example, the provider device 110 can provide an indication which security features of the identification document of the patient 130 are satisfied to the verification server 120. The verification server 120 can then apply one or more eligibility rules to the indication and provide a response of "Eligible to receive services A, B, and C" to the provider device 110 that indicates the patient is eligible to receive services A, B, and C (and not any other service not indicated). In some implementations, the verification server 120 can verify that a service was provided by the provider 112 to the patient 130 based on receiving the indication from the provider device 110. For example, the verification server 120 can determine that the provider 112 must be with the patient 130 at the time the indication is received by the verification server 120, from the provider device 110, as there can be no way for the provider device 110 to obtain images of the identification document of the patient 130 and a biometric of the patient 130 unless the provider 112 is with the patient 130 to provide service.

The process 200 includes providing an indication of the eligibility of the patient to receive service (240). For example, the provider device 110 can display "Eligible to receive services A, B, and C" on a display of the provider device 110 after receiving the indication from the server 120 that the patient is eligible to receive services A, B, and C.

Figure 3:
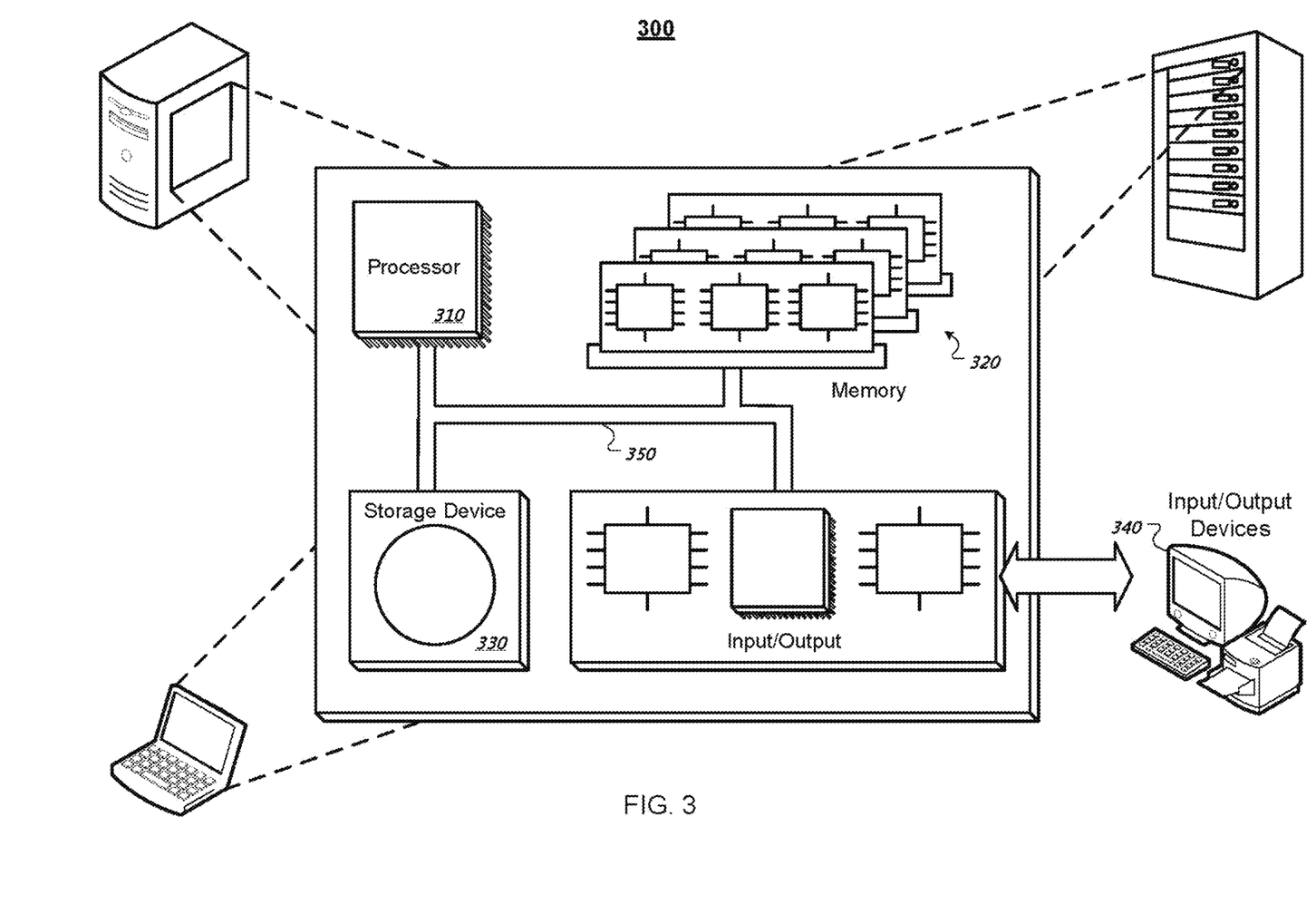
FIG. 3 is a diagram of exemplary computing devices according to implementations of the present disclosure.

FIG. 3 shows an example of a computing device 300 and a mobile computing device 350 that can be used to implement the techniques described here. The computing device 300 is intended to represent various forms of digital computers, such as laptops, desktops, workstations, personal digital assistants, servers, blade servers, mainframes, and other appropriate computers. The mobile computing device 350 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 300 includes a processor 302, a memory 304, a storage device 306, a high-speed interface 308 connecting to the memory 304 and multiple high-speed expansion ports 310, and a low-speed interface 312 connecting to a low-speed expansion port 314 and the storage device 306. Each of the processor 302, the memory 304, the storage device 306, the high-speed interface 308, the high-speed expansion ports 310, and the low-speed interface 312, are interconnected using various busses, and can be mounted on a common motherboard or in other manners as appropriate. The processor 302 can process instructions for execution within the computing device 300, including instructions stored in the memory 304 or on the storage device 306 to display graphical information for a graphical user interface (GUI) on an external input/output device, such as a display 316 coupled to the high-speed interface 308. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 304 stores information within the computing device 300. In some implementations, the memory 304 is a volatile memory unit or units. In some implementations, the memory 304 is a non-volatile memory unit or units. The memory 304 can also be another form of computer-readable medium, such as a magnetic or optical disk.

The storage device 306 is capable of providing mass storage for the computing device 300. In some implementations, the storage device 306 can be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 302), perform one or more methods, such as those described above. The instructions can also be stored by one or more storage devices such as computer- or machine-readable mediums (for example, the memory 304, the storage device 306, or memory on the processor 302).

The high-speed interface 308 manages bandwidth-intensive operations for the computing device 300, while the low-speed interface 312 manages lower bandwidth-intensive operations. Such allocation of functions is an example only. In some implementations, the high-speed interface 308 is coupled to the memory 304, the display 316 (e.g., through a graphics processor or accelerator), and to the high-speed expansion ports 310, which can accept various expansion cards (not shown). In the implementation, the low-speed interface 312 is coupled to the storage device 306 and the low-speed expansion port 314. The low-speed expansion port 314, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 300 can be implemented in a number of different forms, as shown in the figure. For example, it can be implemented as a standard server 320, or multiple times in a group of such servers. In addition, it can be implemented in a personal computer such as a laptop computer 322. It can also be implemented as part of a rack server system 324. Alternatively, components from the computing device 300 can be combined with other components in a mobile device (not shown), such as a mobile computing device 350. Each of such devices can contain one or more of the computing device 300 and the mobile computing device 350, and an entire system can be made up of multiple computing devices communicating with each other.

The mobile computing device 350 includes a processor 352, a memory 364, an input/output device such as a display 354, a communication interface 366, and a transceiver 368, among other components. The mobile computing device 350 can also be provided with a storage device, such as a micro-drive or other device, to provide additional storage. Each of the processor 352, the memory 364, the display 354, the communication interface 366, and the transceiver 368, are interconnected using various buses, and several of the components can be mounted on a common motherboard or in other manners as appropriate.

The processor 352 can execute instructions within the mobile computing device 350, including instructions stored in the memory 364. The processor 352 can be implemented as a chipset of chips that include separate and multiple analog and digital processors. The processor 352 can provide, for example, for coordination of the other components of the mobile computing device 350, such as control of user interfaces, applications run by the mobile computing device 350, and wireless communication by the mobile computing device 350.

The processor 352 can communicate with a user through a control interface 358 and a display interface 356 coupled to the display 354. The display 354 can be, for example, a TFT (Thin-Film-Transistor Liquid Crystal Display) display or an OLED (Organic Light Emitting Diode) display, or other appropriate display technology. The display interface 356 can comprise appropriate circuitry for driving the display 354 to present graphical and other information to a user. The control interface 358 can receive commands from a user and convert them for submission to the processor 352. In addition, an external interface 362 can provide communication with the processor 352, so as to enable near area communication of the mobile computing device 350 with other devices. The external interface 362 can provide, for example, for wired communication in some implementations, or for wireless communication in other implementations, and multiple interfaces can also be used.

The memory 364 stores information within the mobile computing device 350. The memory 364 can be implemented as one or more of a computer-readable medium or media, a volatile memory unit or units, or a non-volatile memory unit or units. An expansion memory 374 can also be provided and connected to the mobile computing device 350 through an expansion interface 372, which can include, for example, a SIMM (Single In Line Memory Module) card interface. The expansion memory 374 can provide extra storage space for the mobile computing device 350, or can also store applications or other information for the mobile computing device 350. Specifically, the expansion memory 374 can include instructions to carry out or supplement the processes described above, and can include secure information also. Thus, for example, the expansion memory 374 can be provided as a security module for the mobile computing device 350, and can be programmed with instructions that permit secure use of the mobile computing device 350. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, instructions are stored in an information carrier that the instructions, when executed by one or more processing devices (for example, processor 352), perform one or more methods, such as those described above. The instructions can also be stored by one or more storage devices, such as one or more computer- or machine-readable mediums (for example, the memory 364, the expansion memory 374, or memory on the processor 352). In some implementations, the instructions can be received in a propagated signal, for example, over the transceiver 368 or the external interface 362.

The mobile computing device 350 can communicate wirelessly through the communication interface 366, which can include digital signal processing circuitry where necessary. The communication interface 366 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 368 using a radio-frequency. In addition, short-range communication can occur, such as using a Bluetooth, WiFi, or other such transceiver (not shown). In addition, a GPS (Global Positioning System) receiver module 370 can provide additional navigation- and location-related wireless data to the mobile computing device 350, which can be used as appropriate by applications running on the mobile computing device 350.

The mobile computing device 350 can also communicate audibly using an audio codec 360, which can receive spoken information from a user and convert it to usable digital information. The audio codec 360 can likewise generate audible sound for a user, such as through a speaker, e.g., in a handset of the mobile computing device 350. Such sound can include sound from voice telephone calls, can include recorded sound (e.g., voice messages, music files, etc.) and can also include sound generated by applications operating on the mobile computing device 350.

The mobile computing device 350 can be implemented in a number of different forms, as shown in the figure. For example, it can be implemented as a cellular telephone 380. It can also be implemented as part of a smart-phone 382, personal digital assistant, or other similar mobile device.

What is claimed is:

1. A system comprising:
   one or more processors; and
   one or more data stores coupled to the one or more processors having instructions stored thereon to provide identity verification which instructions, when executed by the one or more processors, causes the one or more processors to perform operations comprising:
   obtaining, from a first computing device, first identity verification information that includes an image of a provider identification document and a representation of a biometric of a service provider, wherein the first computing device is associated with a patient;
   verifying the service provider by:

obtaining, from a first third party ID verification system, an indication that the provider identification document is authentic, and verifying that the representation of the biometric of the service provider corresponds to a biometric indicated on the provider identification document;

obtaining, from a second computing device, second identity verification information that includes an image of a patient identification document and a representation of a biometric of a patient, wherein the second computing device is associated with the service provider;

verifying the patient by:

obtaining, from a second third party ID verification system, an indication that the patient identification document is authentic, and verifying that the representation of the biometric of the patient corresponds to a biometric indicated on the patient identification document;

in response to verifying the service provider and the patient, determining eligibility of the patient to receive services from the service provider;

in response to determining the eligibility, providing, to the second computing device, access to a record of services to be provided to the patient by the service provider and recording a first time;

obtaining, from the second computing device, an indication that the service provider has completed performing the services and, in response, recording a second time;

in response to obtaining the indication that the service provider has completed performing the services, determining, based on an elapsed time between the first time and the second time, a likelihood that the service provider properly completed all of the services on the record of services; and recording completion of the services.

2. The system of claim 1, wherein the first third party ID verification system is associated with an identification issuing authority that issued the provider identification document and the second third party ID verification system is associated with an identity issuing authority that issued the patient identification document.

3. The system of claim 1, wherein determining the eligibility of the patient to receive the services from the service provider comprises determining that the service provider is qualified to perform the services.

4. The system of claim 1, wherein determining the eligibility of the patient to receive the services from the service provider comprises determining that the patient is approved to receive the services from the service provider.

5. The system of claim 1, wherein providing access to the record of services to be provided to the patient by the service provider comprises:

identifying a role of the service provider, the role corresponding to a skill set of the service provider; and generating, based on the role, a list of services that the patient is due to receive and that correspond to the role of the service provider.

6. The system of claim 1, wherein the operations further comprise providing, to the first computing device, access to the record of services to be provided to the patient by the service provider.

7. The system of claim 1, wherein determining the likelihood that the service provider properly completed all of the services on the record of services comprises:

comparing the elapsed time to an expected time for performing the services; and determining the likelihood based on whether the elapsed time is within a threshold value of the expected time.

8. The system of claim 1, wherein obtaining the indication that the service provider has completed performing the services comprises:

obtaining third identity verification information; and determining that the third identity verification information includes a second image of the provider identification document and a second biometric of the service provider that matches a corresponding biometric on the provider identification document.

9. A system comprising:

one or more processors; and one or more data stores coupled to the one or more processors having instructions stored thereon to provide identity verification which instructions, when executed by the one or more processors, causes the one or more processors to perform operations comprising:

obtaining, from a computing device, first identity verification information that includes an image of a patient identification document and a representation of a biometric of a patient, wherein the computing device is associated with a service provider;

verifying the patient by:

obtaining, from a first third party ID verification system, an indication that the patient identification document is authentic, and verifying that the representation of the biometric of the patient corresponds to a biometric indicated on the patient identification document;

determining that a physical location of the computing device is proximate to a physical location of the patient;

in response to verifying the patient and determining that the physical location of the computing device is proximate to the physical location of the patient, determining eligibility of the patient to receive services from the service provider, wherein eligibility is determined based on a set of eligibility rules that set a minimum standard of confidence for verification of a patient identity in order to permit the provider to perform services;

in response to determining the eligibility, providing, to the computing device, access to a record of services to be provided to the patient by the service provider and recording a first time;

obtaining an indication that the service provider has completed performing the services and, in response, recording a second time;

in response to obtaining the indication that the service provider has completed performing the services, determining, based on an elapsed time between the first time and the second time, a likelihood that the service provider properly completed all of the services on the record of services; and recording completion of the services.

10. The system of claim 9, wherein determining that the physical location of the computing device is proximate to the physical location of the patient comprises comparing GPS data associated with the computing device to an address of the patient indicated on the patient identification document.

11. The system of claim 10, wherein determining that the physical location of the computing device is proximate to the physical location of the patient comprises determining that the GPS data indicates a location that is within a threshold distance of the address.

12. The system of claim 9, wherein determining that the physical location of the computing device is proximate to the physical location of the patient comprises comparing GPS data associated with the computing device to a predetermined physical location of the patient.

13. The system of claim 9, wherein determining that the physical location of the computing device is proximate to the physical location of the patient comprises obtaining, from the computing device, a scan of a machine readable code associated with the physical location of the patient.

14. The system of claim 9, wherein determining that the physical location of the computing device is proximate to the physical location of the patient comprises:
sending, to a second computing device that is associated with the patient, a machine readable code; and
obtaining, from the computing device, a scan of the machine readable code sent to the second computing device.

15. The system of claim 9, wherein determining that the physical location of the computing device is proximate to the physical location of the patient comprises:
obtaining, from a second computing device that is associated with the patient, second identity verification information, the second identity verification information including an image of a provider identification document and a representation of a biometric of the service provider; and
verifying the service provider by:
obtaining, from a second third party ID verification system, an indication that the provider identification document is authentic, and
verifying that the representation of the biometric of the service provider corresponds to a biometric indicated on the provider identification document.

16. The system of claim 9, wherein determining the eligibility of the patient to receive the services from the service provider comprises determining that the service provider is qualified to perform the services.

17. The system of claim 9, wherein determining the eligibility of the patient to receive the services from the service provider comprises determining that the patient is approved to receive the services from the service provider.

18. The system of claim 9, wherein providing access to the record of services to be provided to the patient by the service provider comprises:
identifying a role of the service provider, the role corresponding to a skill set of the service provider; and
generating, based on the role, a list of services that the patient is due to receive and that correspond to the role of the service provider.

19. The system of claim 9, wherein determining the likelihood that the service provider properly completed all of the services on the record of services comprises:
comparing the elapsed time to an expected time for performing the services; and
determining the likelihood based on whether the elapsed time is within a threshold value of the expected time.

20. A computer implemented identity verification method executed by one or more processors, the method comprising:
obtaining, from a computing device, first identity verification information that includes an image of a patient identification document and a representation of a biometric of a patient, wherein the computing device is associated with a service provider;
verifying the patient by:
obtaining, from a first third party ID verification system, an indication that the patient identification document is authentic, and
verifying that the representation of the biometric of the patient corresponds to a biometric indicated on the patient identification document;
determining that a physical location of the computing device is proximate to a physical location of the patient;
in response to verifying the patient and determining that the physical location of the computing device is proximate to the physical location of the patient, determining eligibility of the patient to receive services from the service provider, wherein eligibility is determined based on a set of eligibility rules that set a minimum standard of confidence for verification of a patient identity in order to permit the provider to perform services;
in response to determining the eligibility, providing, to the computing device, access to a record of services to be provided to the patient by the service provider and recording a first time;
obtaining an indication that the service provider has completed performing the services and, in response, recording a second time;
in response to obtaining the indication that the service provider has completed performing the services, determining, based on an elapsed time between the first time and the second time, a likelihood that the service provider properly completed all of the services on the record of services; and
recording completion of the services.

* * * * *